United States Patent [19]

Eckstein et al.

[11] Patent Number: 4,821,711

[45] Date of Patent: Apr. 18, 1989

[54] PROTECTIVE BREATHING DEVICE

[75] Inventors: Wolfgang Eckstein, Friedrich-Ebert-Ring; Wolfgang Drews, Bahrenhof, both of Fed. Rep. of Germany

[73] Assignee: Draegerwerk AG, Fed. Rep. of Germany

[21] Appl. No.: 142,461

[22] Filed: Jan. 7, 1988

[30] Foreign Application Priority Data

Jan. 9, 1987 [DE] Fed. Rep. of Germany ....... 3300458

[51] Int. Cl.⁴ ............................................ A61M 15/00

[52] U.S. Cl. ........................... 128/202.26; 128/204.15

[58] Field of Search ........................ 128/204.15, 202.26

[56] References Cited

U.S. PATENT DOCUMENTS

| | | | |
|---|---|---|---|
| 1,625,419 | 4/1927 | McCaa | 128/204.15 |
| 1,983,475 | 12/1934 | Lemoine | 128/202.26 |
| 4,164,218 | 8/1979 | Martin | 128/202.26 |
| 4,187,843 | 2/1980 | Warncke et al. | 128/202.26 |
| 4,213,453 | 7/1980 | Warncke et al. | 128/202.26 |
| 4,300,547 | 11/1981 | Pasternack | 128/204.15 |
| 4,409,978 | 10/1983 | Bartos | 128/202.26 |
| 4,459,981 | 7/1984 | Mascher et al. | 128/202.26 |
| 4,635,629 | 1/1987 | Thorp et al. | 128/204.15 |
| 4,665,910 | 5/1987 | Kolbe et al. | 128/204.15 |

FOREIGN PATENT DOCUMENTS

| | | | |
|---|---|---|---|
| 3442882 | 5/1986 | Fed. Rep. of Germany . | |
| 1111766 | 9/1984 | U.S.S.R. | 128/204.15 |

*Primary Examiner*—Paul T. Sewell
*Assistant Examiner*—Aaron J. Lewis
*Attorney, Agent, or Firm*—McGlew & Tuttle

[57] ABSTRACT

A protective breathing device with regeneration of the breathed air includes a regeneration cartridge arranged in the flow between a breath intake and a breathing bag. The device provides effective cooling of the inhaled air and the best possible protection of the wearer against touching the heated cartridge while keeping the overall arrangement as compact and easy to wear as possible. For this purpose, a breathing bag 16 is divided into two partial bag, the first being an exhalation pouch containing a regeneration cartridge, which is arranged to force exhaled air into a second partial bag, or inhalation bag through valving the regenerated breathing air is connected back to a breathing mouth piece.

6 Claims, 1 Drawing Sheet

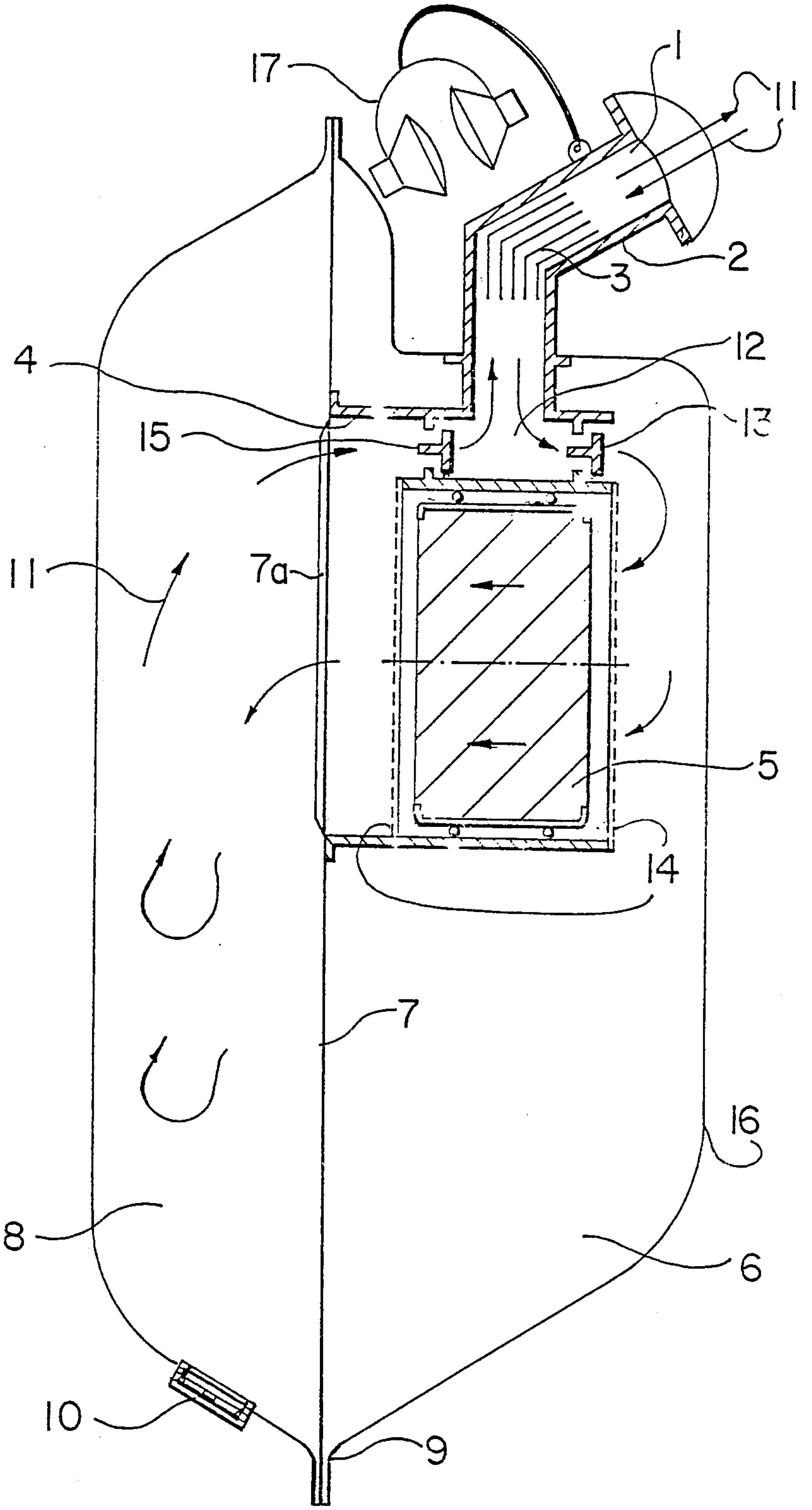
17
1
11
2
3
12
4
13
15
11
7a
5
14
7
16
8
6
10
9

PROTECTIVE BREATHING DEVICE

BACKGROUND OF THE INVENTION

FIELD OF THE INVENTION

The invention relates in general to respirators and in particular to a new and useful protective breathing device with regeneration of the breathed air, whose regeneration cartridge is arranged in an air flow between a breath intake and a breathing bag.

A similar protective breathing device is described in DE-OS No. 34 42 882.

In the known protective breathing device, the exhaled air is guided through a regeneration cartridge into a following breathing bag. During the regeneration, $CO_2$ is bound and oxygen is given off. The heat of the regeneration is liberated, warming the cartridge. In the next inhalation from the breathing bag, the inhaled air is again conveyed from the breathing bag through the cartridge to the mouthpiece (back-and-forth breathing). The inhaled air is warmed by travelling through the cartridge and must therefore be taken across a following cooling surface before being breathed.

A disadvantage of the known device is the fact that only a relatively small surface is available for cooling the heated inhalation air, if the construction of the device is to be as small and light as possible.

When breathing forcefully through the known protective breathing device, the inhaled air is warmed so much that the cooling surface can no longer provide adequate cooling. Moreover, a heavily heated regeneration cartridge is not sufficiently protected against touching from the outside, since the cartridge cannot be covered on all side by the cooling surface.

SUMMARY OF THE INVENTION

The present invention provides an improved protective breathing device having more effective cooling of the inhaled air and more total protection of the wearer against touching the heated cartridge, while keeping the overall device as light and compact as possible.

According to the invention, the breathing bag is divided into two partial pouches, the first as the exhalation bag containing a regeneration cartridge, which in order to force the exhaled air into the second partial bag is configured as the inhalation bag. The exhalation bag is connected to the second bag by the air flow. The principal advantage of the invention is having the cartridge in the exhalation bag so that, not only does the exhaled air flow through the cartridge for regeneration during the exhalation, but the cartridge is also washed by comparatively cooler exhaled air during the exhalation, so that a cooling of the outer housing of the cartridge is also achieved, and the fact of its being surrounded by the exhalation bag provides good protection against touching it.

Also, after the exhaled air moves through the cartridge into the inhalation bag a satisfactory cooling of the warmed exhaled air is achieved, thanks to the large outer surface of the inhalation bag.

A further advantage lies in the fact that, by accommodating the regeneration cartridge in the breathing bag, the overall volume of the breathing bag need not be much enlarged, so that greater wearing comfort is achieved.

Easy loading of the regeneration cartridge can be accomplished in a housing which is attached to the partition wall of the breathing bag and which contains the inhalation and exhalation valve. With this expedient measure, the breathing bag can be carried by the housing, without requiring a special suspension.

Preferably the breath intake emerges into an antechamber of the housing, in which the exhalation and inhalation valve are arranged. In this manner, one achieves an especially small size of the housing of the cartridge, so that the protective breathing device can be easily carried by the mouthpiece, without an additional strap.

For better cooling capability, there are cooling fins in the mouthpiece tube.

Accordingly it is an object of the invention to provide a breathing device which includes an air impermeable bag with a partition wall extending completely through the bag and dividing it into an exhalation bag portion on one side of the partition wall and an inhalation bag portion on the opposite side and wherein, breathing housing assembly is mounted in the pouch on the partition wall and it includes a regenerative cartridge in the bag and a breathing tube connection extending out of the bag and defining a valve inhalation passage extending from the interior of the inhalation bag through the breathing tube connection and a valve exhalation passage which extends from the breathing tube connection through the exhalation bag and through the regenerative cartridge to the inhalation bag.

A further object of the invention is to provide a protective breathing device which is simple in design, rugged in construction and economical to manufacture.

A further object of the invention is to provide a method of operating a breathing device using a bag which has a division wall therein, dividing it into an exhalation bag chamber and an inhalation bag chamber and a separate housing for respiration which includes a connection for breathing extending from the exterior of the bag to the interior one passage feeding through a valve opening into a regenerative cartridge and to the inhalation bag and the return passage from the inhalation bag feeding through a valve opening directly to the breathing tube and which comprises exhaling air through the breathing tube past a valve and into the exhalation bag chamber portion and then through a regenerative cartridge through the inhalation bag portion and inhaling air so that it is withdrawn from the inhalation bag portion through a valve passage through the breathing passage and the user.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention is illustrated.

BRIEF DESCRIPTION OF THE DRAWINGS

In the drawings:

The only FIGURE of the drawings is a sectional view through a breathing device constructed in accordance with the invention.

GENERAL DESCRIPTION OF THE PREFERRED EMBODIMENTS

Referring to the drawings in particular the invention embodied therein comprises a protective breathing device which includes an air impermeable bag 16 having a partition wall 7 therein, which extends completely through the bag and has an exhalation opening *7a*. The partition wall 7 divides the bag into an exhalation bag chamber 6 on one side of the partition wall, and an inhalation bag chamber 8 on the opposite side. A breathing housing assembly 4 is mounted in the bag on the partition wall 7 and has a breathing air regenerative cartridge 5, which is positioned in the exhalation bag portion 6. The housing 4 also includes a breathing tube part for mouthpiece 2 extending out of the exhalation bag portion 6 and terminating in a mouthpiece 1. The housing 4 also defines a valve inhalation passage in the mouthpiece 2 which extends through an inhalation valve 15 and the opening *7a* from the inhalation bag portion 8. In addition, the housing 4 with the bag defines a valve exhalation passage from the mouthpiece 2 through an exhalation valve 13 and the exhalation bag portion 6 and through the regenerator 5 to the inhalation bag portion 8.

The single drawing shows a protective breathing device in sectional view, which has a mouthpiece 1, connected to a housing 4 for accommodation of a regeneration cartridge 5 across a mouthpiece tube 2, provided with cooling fins 3. The housing 4 is enveloped in an exhalation bag or partial bag 6, which is placed about the mouthpiece tube 2. The exhalation bag 6 is separated from an inhalation bag or partial bag 8 by a partition wall 7. The inhalation bag 8 and exhalation bag 6 are joined together into a breathing bag or combined bag 16 by a heavy seam 9, the partition wall 7 being included in the seam 9. The inhalation bag 8 contains an outlet valve 10. The housing 4 is secured to the partition wall 7 in such a way that a circulation connection for the inhaled and exhaled air is produced in the directions shown by the various arrows 11. The exhaled air flowing across the mouthpiece 1 and the mouthpiece tube 2 into an antechamber 12 of the housing 4 enters the exhalation bag 8 through an exhalation valve 13, and from there enters the inhalation bag 8 through the regeneration cartridge 5. The regeneration cartridge 5 is held between the two perforated respective front and rear walls 14 of the housing 4. Upon inhalation, the inhaled air returns from the inhalation bag 8 to the antechamber 12 after going through the inhalation valve 15 and from there it is taken back into the mouthpiece 1 to the (not shown) wearer. A nose clamp 17 is placed by the wearer on his nostrils when using the protective breathing device.

While specific embodiments of the invention have been shown and described in detail to illustrate the application of the principles of the invention, it will be understood that the invention may be embodied otherwise without departing from such principals.

What is claimed is:

1. A protective breathing device comprising an air impermeable bag, a partition wall extending completely through said bag having an exhalation opening therethrough, said partition wall dividing said bag into an exhalation chamber on one side and an inhalation chamber on the opposite side, a breathing housing assembly mounted in said bag exhalation chamber portion on said partition wall and having a breathing air regeneration cartridge in said exhalation chamber portion and a breathing tube connection extending out of said bag and having an offset portion terminating in a mouthpiece which forms a part of said housing and including a plurality of spaced parallel cooling fins located in said breathing tube passage, said breathing tube connection and said housing defining a valved inhalation passage extending from the interior of said inhalation chamber through said partition wall exhalation opening and through said valve passage to the exterior and also defining a valved exhalation passage extending from the exterior of said bag through said valved exhalation passage into said inhalation chamber, said housing including a two-way passage below said breathing tubes located in said exhalation chamber having respective inhalation and exhalation passages that are at opposite ends, said exhalation passage communicating with a passage adjecent said partition wall opening for feeding inhaled air backwardly from said inhalation chamber through said breathing passage wherein, the opposite end of said passage includes an exhalation valve opening into said exhalation chamber of said bag.

2. A protective breathing device according to claims 1 wherein, said valve inhalation passage includes an inhalation valve which open during inhalation and said valved exhalation passage includes a exhalation valve which opens during exhalation.

3. A protective breathing device according to claim 1 wherein said regenerative cartridge lies within said housing, said housing has a perforated wall on each side of said regenerative cartridge.

4. A protective breathing device, comprising a breathing pouch, a wall dividing said pouch into first and second pouch compartments having a communication opening therebetween, means defining a housing assembly around said opening in said second pouch compartment and a breathing gas passage from said housing assembly to the exterior of said breathing pouch, a breathing gas regeneration cartridge in said housing assembly, first and second valve passages connected to said breathing gas passage permitting exhalation flow from said gas passage into said second pouch compartment through said cartridge opening into said first compartment, and also permitting inhalation air flow from said first compartment through said opening and directly into said breathing gas passage said housing further including a two-way passage located in said exhalation chamber having respective inhalation and exhalation passages that are at opposite ends, said exhalation passage communicating with a passage adjacent said partition wall opening for feeding inhaled air backwardly from said first valve breathing passage wherein, the opposite end of said passage includes a second valve passage opening into said exhalation chamber of said bag.

5. A protective breathing device according to claim 4, wherein said first and second valve passages comprise a transversely extending air flow passage connected to a breathing tube forming a passage extending at an angle to said transverse passage, said transverse passage having a valve opening under exhalation pressure at one end and a valve opening under inhalation pressure at its opposite end.

6. A protective breathing device according to claim 4 wherein said housing includes a breathing tube having an offset portion terminating in a mouthpiece which forms a part of said housing and including a plurality of spaced parallel cooling fins located in said breathing tube.

* * * * *